United States Patent [19]
Tarasova et al.

[11] Patent Number: 5,679,663
[45] Date of Patent: Oct. 21, 1997

[54] PHARMACEUTICAL COMPOUNDS

[75] Inventors: Raisa Ivanovna Tarasova; Valeriy Arkadjevitch Pavlov; Viktor Vladimirovich Moskva; Irina Ivanovna Semina, all of Kazan, Russian Federation

[73] Assignee: British Technology Group Limited, London, England

[21] Appl. No.: 676,110

[22] PCT Filed: Jan. 10, 1994

[86] PCT No.: PCT/IB94/00009

§ 371 Date: Sep. 25, 1996

§ 102(e) Date: Sep. 25, 1996

[87] PCT Pub. No.: WO95/18810

PCT Pub. Date: Jul. 13, 1995

[51] Int. Cl.$^6$ ............................ A61K 31/66; C07F 9/32
[52] U.S. Cl. ............................ 514/119; 558/154
[58] Field of Search .................... 514/119; 558/154

[56] References Cited

U.S. PATENT DOCUMENTS 4,162,311  7/1979  Razumov et al. .

OTHER PUBLICATIONS

Ismagilov, R.K. et al "Synthesis and biological activity . . . " Khim–Farm ZH. (Khfzan, 00231134); 1982 vol. 16 (3); pp.296–300.

Razumov A.I. et al "Derivatives of phosphinic and phosphinous acids . . . " ZH. Obshich. Khim. (Zokha4); 1967; vol. 37 (2); pp. 421–424.

Zhuravleva, G.G. et al "Synthesis and biological activity of phosphorylated carboxylic acid . . . " Khim–Farm ZH. (Khfzan, 00231134); 1978 vol. 12 (4); pp.79–83.

Semina, I.I et al "Synthesis and neurotropic activity of diarylphosphorylacetyl . . . " Khim–Farm ZH. (Khfzan, 00231134); 1991 vol. 25 (5); pp.45–46.

Primary Examiner—Johann Richter
Assistant Examiner—Michael G. Ambrose
Attorney, Agent, or Firm—Nixon & Vanderhye

[57] ABSTRACT

Compounds of formula (I)

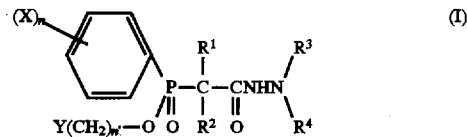

wherein each X separately is halogeno, hydroxy, $C_{1-4}$ alkyl, $C_{1-4}$ alkoxy, nitro or an unsubstituted or substituted amino group NRR' in which R and R' are each separately selected from hydrogen, $C_{1-4}$ alkyl groups and $C_{2-4}$ halogenated alkyl groups;

wherein Y is halogeno, hydroxy, $C_{1-4}$ alkoxy or an unsubstituted or substituted amino group NRR' in which R and R' are as defined above;

wherein n represents 0, 1, 2 or 3 and n' represents 1, 2, 3 or 4;

wherein $R^1$ and $R^2$ each separately represent hydrogen, halogeno, phenyl or a $C_{1-4}$ alkyl group, or together represent a group =NOR'' in which R'' is hydrogen or is a group ZC(O)— or $(ZO)_2P(O)$— where Z is a $C_{1-4}$ alkyl group; and wherein $R^3$ and $R^4$ each separately represent hydrogen, acetyl, phenyl, 2,2,2-trichloro-1-hydroxyethyl or a $C_{1-4}$ alkyl group, or together represent a group =CHR''' in which R''' is a $C_{1-4}$ alkyl, $C_{1-4}$ halogenated alkyl or phenyl group or represent a group =CH—CH=CHR''' in which R''' is as defined above; the compound or its physiologically acceptable salt, are of value in the treatment of depression and/or in memory enhancement.

19 Claims, 2 Drawing Sheets

PHARMACEUTICAL COMPOUNDS

This application was filed under 35 U.S.C. 371 and was based upon International Application No. PCT/IB94/00009, filed Jan. 10, 1994.

The invention relates to hydrazides of phosphorylated carboxylic acids having therapeutic activity, particularly in treating depression and for effecting memory enhancement.

Razumov et al., Zhurnal obshchei khimii, 1967, vol. 37, 421–424 describe hydrazides of phosphorylated carboxylic acids of structure $R_1R_2P(O)CH_2C(O)NHNH_2$ in which $R_1$ and $R_2$ are selected from phenyl, p-tolyl, ethyl, ethoxy and butoxy groups and N-substituted derivatives thereof. These hydrazides were reported as showing a low level of antimicrobial activity. U.S. Pat. Nos. 4,162,264 and 4,162,311 describe a hydrazide of diphenylphosphinylacetic acid [diphenylphosphinylacetohydrazide, hereinafter "DPAH", $(C_6H_5)_2P(O)CH_2C(O)NHNH_2$] which has vegetropic, anti-epileptic and anti-serotonin properties. Hydrazides of phosphorylated acetic acids, which display a low level of neurotropic activity, are also described by Ismagilov et al., Khim.-Farm. Zhurnal, 1982, 16, 296–300 and Zhuravleva et al., Khim.-Farm. Zhurnal, 1978, vol. 12, 79–93 (both also published in English translation).

It is well known that patients who suffer from neurodegenerative diseases, for example Alzheimer's disease and Parkinson's disease, or, as a result of a stroke or head injury or merely as the result of advancing age, suffer from memory-loss, often also have symptoms ranging from mild anxiety to severe depression. Such patients respond to treatment with neuroprotective agents and in particular memory-enhancing drugs (so-called "cognitive enhancers") and anti-depressants.

It is an object of the present invention to expand the arsenal of remedies available for use in these areas and it has now been found, for example, that the novel compound (2-chloroethoxy)-(p-N,N-dimethylaminophenyl) phosphinylacetohydrazide [formula] (I), X=p—$(CH_3)_2N$, Y=Cl, n=1, n'=2, $R^1=R^2$=H and $R^3$=$R^4$=H] is a potent neuroprotective agent and in particular displays anti-depressant and memory enhancing activity.

Accordingly the present invention comprises a compound having the following general formula (I):

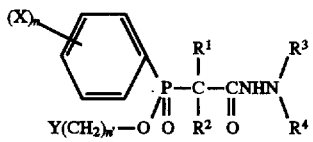

wherein each X separately is halogeno, hydroxy, $C_{1-4}$ alkyl, $C_{1-4}$ alkoxy, nitro or an unsubstituted or substituted amino group NRR' in which R and R' are each separately selected from hydrogen, $C_{1-4}$ alkyl groups and $C_{2-4}$ halogenated alkyl groups;

wherein Y is halogeno, hydroxy, $C_{1-4}$ alkoxy or an unsubstituted or substituted amino group NRR' in which R and R' are as defined above;

wherein n represents 0, 1, 2 or 3 and n' represents 1, 2, 3 or 4;

wherein $R^1$ and $R^2$ each separately represent hydrogen, halogeno, phenyl or a $C_{1-4}$ alkyl group, or together represent a group =NOR" in which R" is hydrogen or is a group ZC(O)— or (ZO)$_2$P(O)— where Z is a $C_{1-4}$ alkyl group; and wherein $R^3$ and $R^4$ each separately represent hydrogen, acetyl, phenyl, 2,2,2-trichloro-1-hydroxyethyl or a $C_{1-4}$ alkyl group, or together represent a group =CHR''' in which R''' is a $C_{1-4}$ alkyl, $C_{1-4}$ halogenated alkyl or phenyl group or represent a group =CH—CH=CHR''' in which R''' is as defined above, with any phenyl group present in $R^3$, $R^4$ or $R^3$+$R^4$ optionally being substituted by 1 to 3 groups selected from halogeno, hydroxy, $C_{1-4}$ alkyl, $C_{1-4}$ alkoxy, nitro and unsubstituted or substituted amino groups NRR' in which R and R' are as defined above; the compound optionally being in the form of a physiologically acceptable salt.

In the compounds (I) halogeno groups are preferably iodo, bromo, or especially chloro and the $C_{1-4}$ alkyl and alkoxy groups may comprise alkyl groups which are branched or preferably straight chain such as methyl, ethyl, propyl, isopropyl, butyl and isobutyl, with the smaller groups such as methyl being of particular interest. Halogenated alkyl groups are constituted of such halogeno and alkyl groups, such groups preferably containing one halogeno group and with the $C_{2-4}$ halogenated alkyl groups preferably being substituted on a carbon atom other than the α carbon atom of the alkyl group, as for example in 2-chloroethyl.

As regards the group $(X)_n$, n is preferably either 0, in which case the phenyl group in the compound (I) is unsubstituted or, more conveniently, n is 1. When n is other than 0, for example 1, X is preferably halogeno or especially NRR'. Disubstituted amino NRR' groups are preferred, for example dialkylamino groups such as dimethylamino. Although the substituent(s) X may be present at various positions of the ring it is preferred that the substituent, or at least one substituent where more than one is present, is at the para position of the benzene ring with respect to the phosphorus-containing grouping.

As regards the group Y this is preferably a halogeno group and n' is conveniently 4, 3 or especially 2 (compounds in which n' is 1 being of less interest particularly when Y is other than halogeno) so that a preferred grouping Y(CH$_2$)$_n$'O— is 2-chloroethoxy. The groups $R^1$ and $R^2$ conveniently are each hydrogen although there is also interest in compounds in which each is halogeno or one is hydrogen and the other is halogeno, phenyl or alkyl, for example methyl, as well as the groups =NOR".

As regards $R^3$ and $R^4$, $R^3$ is preferably hydrogen or together with $R^4$ represents a divalent group. Examples of various specific groups NR$^3$R$^4$ have $R^3$=$R^4$=H; $R^3$=H and $R^4$=COCH$_3$, C$_6$H$_5$, CH(OH)CCl$_3$ or especially CH$_3$ or C$_2$H$_5$; and $R^3$+$R^4$=CHCH$_3$, CHCH$_2$Cl, CHCH=CHCH$_3$, CHCH=CHC$_6$H$_5$ or CHC$_6$H$_5$ as well as such groups $R^4$ and $R^3$+$R^4$ containing a benzene ring in which there is substitution in the benzene ring by one or more halogeno, hydroxy, $C_{1-4}$ alkyl, $C_{1-4}$ alkoxy, nitro and unsubstituted or substituted amino groups NRR', for example $R^4$ being or $R^3$+$R^4$ containing a group which is 2-HOC$_6$H$_4$, 2,4-(HO)$_2$C$_6$H$_4$, 4-CH$_3$OC$_6$H$_4$, 2,4-(CH$_3$O)$_2$C$_6$H$_3$, 4-(CH$_3$)$_2$NC$_6$H$_4$, 4-ClC$_6$H$_4$, 2,4-Cl$_2$C$_6$H$_3$, 2-NO$_2$C$_6$H$_4$, 3-NO$_2$C$_6$H$_4$ or 4-NO$_2$C$_6$H$_4$.

Examples of specific types of compound (I) are those in which NR$^3$R$^4$ is NHCH(OH)CCl$_3$, N=CH—CH=CHCH$_3$, N=CH—CH=CHC$_6$H$_5$, N=CH—C$_6$H$_4$—NO$_2$ (meta), N=CH—C$_6$H$_4$—OH (ortho) or especially NH$_2$. In preferred compounds (I) such a group NR$^3$R$^4$ is combined with $R^1$=R$^2$=hydrogen, n being 0 or X being dimethylamino with n being 1, especially at the para position, and Y(CH$_2$)$_n$'O being a halogenoalkoxy group, especially a group in which n' is 2 such as 2-chloroethoxy.

The most preferred compound is 2-chloroethoxy-(p-N,N-dimethylaminophenyl)phosphinylacetohydrazide, hereinafter referred to as CAPAH and its physiologically acceptable salts, such as the hydrochloride.

The compounds (I) in which $R^3$ and $R^4$ are each hydrogen may be synthesised through the reaction of hydrazine, usually as the hydrate, with a corresponding phosphoryl acetic acid ester. In preferred such esters, the ester grouping —$COOR_3$ corresponding to the grouping —$CONHNR^3R^4$ of the compound (I) contains a group $R_3$ which is a $C_{1-4}$ alkyl group, for example methyl or ethyl. Such ester intermediates are conveniently obtained using the general method described by Arbuzov et al., News of the USSR Academy of Sciences, Chemical Sciences Department, 1952, 854–859 and by Henning et al., J. Prakt. Chem., 1965, 29, 86–92 in which an ester of the corresponding phenyl phosphonous acid is reacted with an appropriate alkyl haloacetate. Compounds (I) in which one or both of $R^3$ and $R^4$ are not hydrogen may be prepared directly by the use of an alternative reagent to hydrazine or alternatively may be prepared by the further reaction of the compound in which $R^3$ and $R^4$ are each hydrogen with the appropriate reagent. Thus, for example a grouping $NR^3R^4$ of the form NHCH(OH)$CCl_3$ may be produced using trichloroacetaldehyde and the groups N=CH—CH=CHCH$_3$ and N=CH—CH=CHC$_6$H$_5$, for example, may be produced using crotonaldehyde and cinnamaldehyde, respectively.

In an alternative procedure, CAPAH and its analogues in which $Y(CH_2)_n$'O is a halogeno-ethoxy group may be prepared by way of a "one pot synthesis" by reacting p-N,N-dimethylphenyldichlorophosphine with ethylene oxide and subsequently treating the reaction product with ethyl chloroacetate and hydrazine hydrate or another ester $XCH_2COOR$ in which X is a halogeno group and R is an alkyl group, for example of 1–4 carbon atoms. This procedure, which is based on that described in U.S. Pat. No. 4,162,264 for the preparation of the compound $(C_6H_5)_2P(O)CH_2C(O)NHNH_2$, effects the following reaction scheme A.

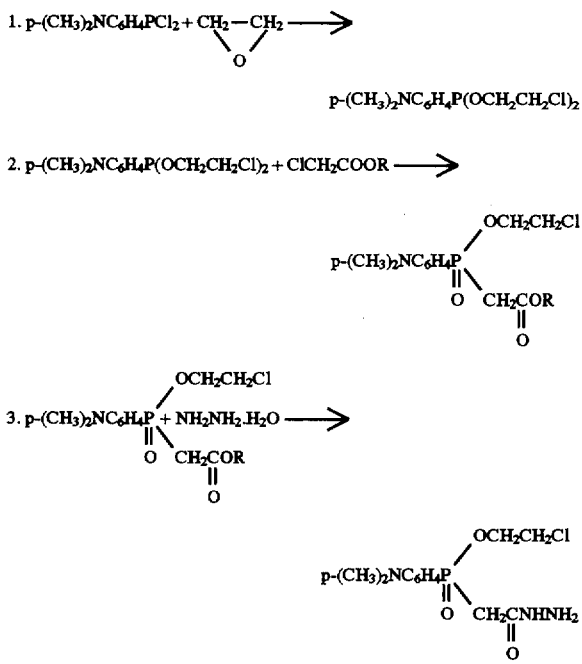

The initial reactant, para-N,N-dimethylaminophenyldichlorophosphine is obtained by a known method (V. V. Kormachev, S. N. Chalykh, V. P. Pavlov & V. A. Kukhtin, "Syntheses based on 4-N,N-dimethylaminophenyldichlorophosphine", Fosfororganicheskie soedineniya i polimery [Organophosphorous compounds and polymers], Collected articles, Chuvashia State University, Cheboksary, 1976, p.119).

Other procedures known to those skilled in the art of chemical synthesis may also be applied to the synthesis of the compounds of use in the present invention.

Firstly, compounds in which Y is a group other than a halogeno group such as a disubstituted amino group may be prepared through the use of the procedure illustrated in the following reaction scheme B for the preparation of the compound (2-N,N-dimethylaminoethoxy)(p-N,N-dimethylaminophenyl)phosphinylacetohydrazide.

Reaction Scheme B

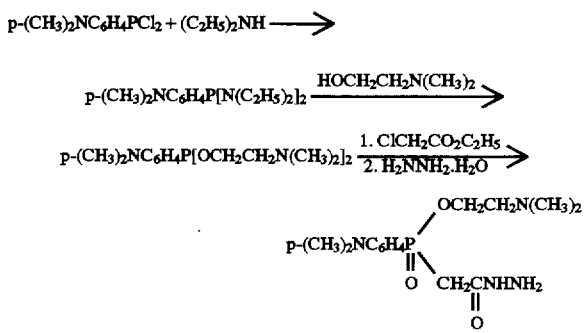

In the first step four molar equivalents of diethylamine are used with the formation in the reaction of two molar equivalents of diethylamine hydrochloride.

Secondly, compounds in which $R^1$ and $R^2$ together represent a group=NOH may be prepared through the use of the procedure illustrated in the following reaction scheme C for the preparation of the compound [(2-chloroethoxy)(p-tolyl)phosphinyl](hydroxyimino)-acetohydrazide.

Reaction Scheme C

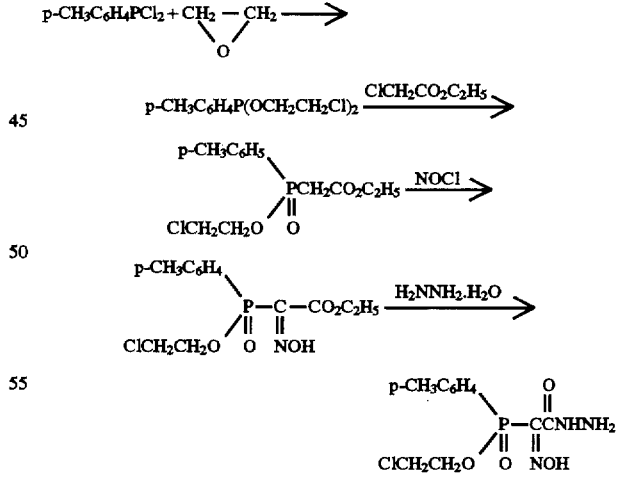

As indicated hereinbefore, the compounds of the invention have been found to have a valuable therapeutic action as anti-depressant and memory enhancing agents.

Accordingly the invention further comprises the compounds of formula (I) as defined hereinbefore for use in therapy.

The invention also includes pharmaceutical compositions comprising as an active component a compound of formula (I) as described hereinbefore together with a physiologically acceptable diluent or carrier.

As indicated, the compounds may be formulated as salts together with physiologically acceptable inorganic or organic acids, there being particular interest in the salts of compounds in which $R_1=R_2=$hydrogen. These may, for example, be salts with the hydrohalic acids such as hydrochloric acid but when so formulated it may also be appropriate to use methane sulphonic acid, isethionic acid, tartaric acid or another solubilising acid.

The compounds of formula (I) may be formulated singly or as a mixture of two or more compounds for use in a pharmaceutical composition by a variety of methods.

The pharmaceutical composition of the invention may be in a form suitable for oral use, for example a tablet, capsule, aqueous or oily solution, suspension or emulsion; for nasal use, for example a snuff, nasal spray or nasal drops; for vaginal or rectal use, for example a suppository; for administration by inhalation, for example a finely divided powder or a liquid aerosol; for sub-lingual or buccal use, for example a tablet or capsule; or for parenteral use (including intravenous, subcutaneous, intramuscular, intravascular or infusion), for example a sterile aqueous or oily solution or suspension. In general, the above compositions may be prepared in a conventional manner using conventional excipients, using standard techniques well known to those skilled in the art of pharmacy.

The compounds of the invention find use in the treatment of clinical depression, particularly reactive depression although they may also be of use in the treatment of manic depression and schizophrenia, and also in the treatment of memory-impaired individuals. A particular advantage of the compounds of the invention is that they combine memory enhancing, anti-depressant, anxiolytic and neuroprotective properties. Hence the pharmaceutical composition of the invention is especially useful in patients suffering from combinations of these symptoms. Thus one particular area of use is as a combined memory enhancer and anti-depressive or anti-anxiety agent, particularly after ischaemia, although another area of use is simply as an anti-depressant. A further potential use which may be mentioned is for correction of sedative effects of benzodiazepine tranquillizers and for treatment of complications induced by neuroleptic drugs.

It will be appreciated that the dosage levels used may vary over a wide range depending on the activity of the particular compound used, the individual patient who is receiving the composition and the condition being treated. By way of guidance, however, it may be indicated that for any of these treatments the compounds of the invention will often be administered at a total dose for a 70 kg human being of between 1 and 1,000 mg daily, especially between 10 and 300 mg daily, although the precise dosage will depend on the particular individual and may on occasion fall outside this range. Where the compound is used purely as an anti-depressive, rather than with a combined memory enhancer effect, the dosages are likely to be somewhat higher in the range than for the combined effect treatment.

The present invention thus includes a method for the treatment of a patient suffering from depression or in need of memory enhancement which comprises administering to said patient a therapeutically effective amount of a compound of formula (I) as defined hereinbefore.

Furthermore the invention includes the use of a compound of formula (I) for the manufacture of a medicament for use in treating depression and/or for effecting memory enhancement.

The invention is illustrated by way of example only with reference to the following drawings, in which.

EXAMPLE 1

Figure 1:
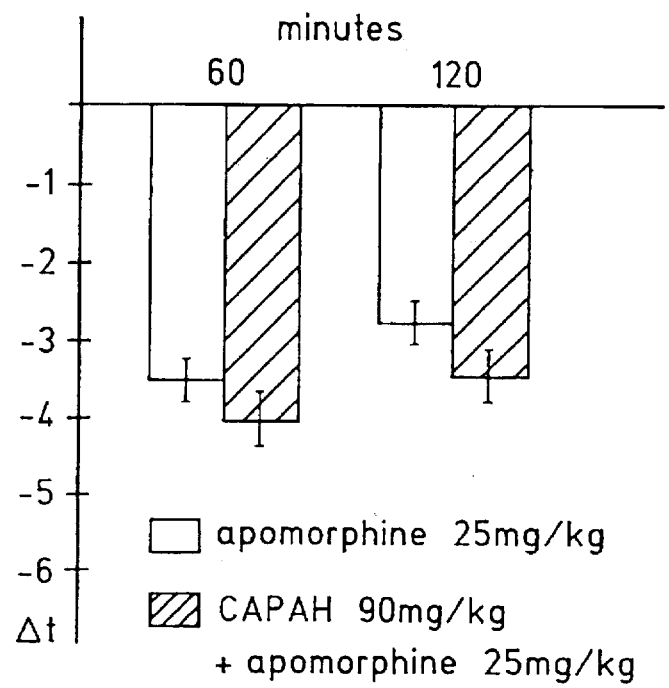
FIG. 1 shows the effect of CAPAH on apomorphine-induced hypothermia in mice.

Synthesis of 2-chloroethoxy(phenyl) phosphinylacetohydrazide (A) To stirred ethyl 2-chloroethoxy(phenyl)phosphinylacetate[1] (0.1 mole) was added hydrazine hydrate (0.3 mole) at room temperature. The reaction mixture was then kept at room temperature for 12–24 hours after which time the resultant solid was filtered off, washed with ethanol:ether (1:1 v/v) and recrystallized from ethanol to give the title compound in 56% yield as white crystals of melting point 159°–160° C. Found, P 11.13%, N 9.84%; Calculated for $C_{10}H_{14}ClN_2O_3P$: P 11.21%, N, 10.12%. $\delta^{31}P$ (dimethyl sulphoxide) 40.5 ppm.

(1) The ethyl 2-chloroethoxy(phenyl)phosphinylacetate was obtained by the general procedure of Arbuzov et al., News of the USSR Academy of Sciences, Chemical Sciences Department, 1952, 854–859 and Henning et al., J. Prakt. Chem., 1965, 29, 86–92 which involves reaction of the corresponding ester of the phenylphosphonous acid with an appropriate alkyl haloacetate.

(B) The procedure described under (A) may be applied, using intermediates obtained as described in the footnote, to the preparation of various compounds of formula (I), for example the corresponding p-chloro, p-methyl and p-dimethylamino substituted compounds.

EXAMPLE 2

Synthesis of CAPAH [(2-chloroethoxy)(p-N,N-dimethylaminophenyl)phosphinylacetohydrazide]

(1) A four-necked flask fitted with a thermometer, gas intake pipe, agitator and reflux condenser was filled with 30.6 g (0.137 mole) of p-N,N-dimethylaminophenyldichlorophosphine and 22.3 g (0.206 mole) methyl chloroacetate. After dissolving the p-N,N-dimethylaminophenyldichlorophosphine, the flask contents were cooled to 0°, and, at a temperature of 0°–100°, 12.05 g (0.274 mole) of ethylene oxide was admitted. The reaction complete, the reaction mixture was heated to room temperature, agitated for ½ hour and the excess ethylene oxide was removed in the vacuum of a water-jet pump. The reflux condenser was then replaced with a Liebig condenser and the reaction mixture slowly heated and vigorously stirred. The reaction proceeded at 100°–110° and was completed in three to four hours. At the end of the reaction, the temperature was raised to 120° C. and held there for 15–20 minutes. The reaction mixture was then cooled to 100°, the dichloroethane and unreacted methyl chloroacetate were distilled off in a vacuum at a residual pressure of 10–15 mm Hg. To the resultant mixture $_{6.84}$ g (0.274 mole) of hydrazine hydrate was added in small portions at room temperature, while stirring. In two hours the reaction mass crystallised. The crystals were filtered off, rinsed first in alcohol then in ether and dried in air. Thus CAPAH was obtained (28.0 g, 63%) as white crystals of melting point 143°–148° C.

After recrystallisation from chloroform, 24.6 g (55%) of pure CAPAH was obtained of melting point 155°–156° C. Found: P 9.20, 9.31%; N 13.50, 13.31%. Calculated for $C_{12}H_{19}ClN_3O_3P$: P 9.70%, N 13.14%. $v_{max}$ (KBr disc) 1197

(P=O), 1650 (NH), 1695 (C=O), 3220–3315 (NH) cm$^{-1}$. $\delta^{31}$P(dimethyl sulphoxide) 40.0 ppm.

(2) In a first variant of the procedure described under (1) the p-N,N-dimethylaminophenyldichlorophosphine is replaced by an equimolar amount of p-chlorophenyldichlorophosphine or p-tolyldichlorophosphine to provide (2-chloroethoxy)(p-chlorophenyl)-phosphinylacetohydrazide or (2-chloroethoxy)(p-tolyl)phosphinylacetohydrazide.

(3) In a second variant of the procedure described under (1) the hydrazine is replaced by an equimolar amount of phenylhydrazine to provide N$^\beta$-(phenyl)-(2-chloroethoxy) (p-N,N-dimethylaminophenyl)-phosphinylacetohydrazide.

EXAMPLE 3

Synthesis of CAPAH Hydrochloride

To a solution of 0.005 mole of CAPAH in 10 ml of ethanol was added an equivalent of hydrogen chloride dissolved in ethanol (8% w/v). The ethanol was removed under vacuum at room temperature and the resulting oil was crystallised. The crystals were filtered from the residual liquid and washed with ether to provide CAPAH hydrochloride in 86% yield as white crystals of m.p. 171° C. having a high water solubility. Found: P 8.75, 8.85%; N 11.50, 11.75%; Cl 19.99, 20.34%. Calculated for $C_{12}H_{20}Cl_2N_3O_3P$: P 8.72%; N 11.78%; Cl 19.94%. $\delta^{31}$P ($H_2O$) 33.8 ppm.

EXAMPLE 4

Synthesis of N$^\beta$-(2,2,2-trichloro-1-hydroxy)-(2-chloroethoxy)(p-N,N-dimethylaminophenyl) phosphinylacetohydrazide To a suspension of 0.005 mole of CAPAH in 5 ml of dry chloroform at room temperature 0.007 mole of trichloroacetaldehyde was added in portions with stirring. The temperature of the reaction mixture increased to 35° C. by the end of the reaction. On completion of the reaction the reaction mixture was stirred at room temperature for 3 hours and the solvent was then removed under vacuum. The resultant oil was purified by several precipitations from hexane to provide the title compound in 52% yield as pale yellow crystals of melting point 115°–116° C. Found: P$_{6.25,}$ $_{6.35}$%; N 8.80, 8.62%. Calculated for $C_{14}H_{20}Cl_4N_3O_4P$: P $_{6.66}$%; N 9.00%. $\delta^{31}$P (dimethyl sulphoxide) 36.7 ppm.

EXAMPLE 5

Synthesis of N$^\beta$-(but-2-enylidene)-(2-chloroethoxy)-(p-N,N-dimethylaminophenyl)phosphinylacetohydrazide and related compounds (A) To a suspension of 0.005 mole of CAPAH in 5 ml of dry chloroform at room temperature was added 0.007 mole of crotonaldehyde in 2 ml of chloroform in portions with stirring. As the reaction proceeded the temperature of the reaction mixture increased to 26°–30° C. until the CAPAH was completely dissolved. The reaction mixture was maintained at room temperature for 6 to 12 hours and the solvent was then removed under vacuum. The resulting oil was purified by several reprecipitations from hexane to provide the title compound as a yellow powder in 67% yield of melting point 145°–146° C. Found: P 8.20%; N 11.57%. Calculated fort $C_{16}H_{24}ClN_3O_3P$: P 8.36%; N 11.30%. $\delta^{31}$P (dimethyl sulphoxide) 37.5, 38.5 ppm.

The compound was poorly soluble in most organic solvents and in water but soluble in dimethyl sulphoxide and other aprotic polar solvents. The two $^{31}$P n.m.r. signals indicate the presence of syn and anti isomeric forms.

(B) The procedure described under (A) above was repeated using cinnamaldehyde, m-nitrobenzaldehyde or salicylaldehyde in place of crotonaldehyde to produce the N$^\beta$-cinnamaylidene, N$^\beta$-m-nitrobenzylidene and N$^\beta$-o-hydroxybenzylidene compounds with the properties indicated in Table 1 below. The solubility of these compounds is similar to that of the compound described under (A).

TABLE 1

| N$^\beta$ Substituent | Yield % | Melting Point °C. | Found % P | Found % N | Calculated % P | Calculated % N | $\delta^{31}$P (CH$_3$)$_2$SO |
|---|---|---|---|---|---|---|---|
| $C_6H_5CH=CH-CH=$ | 83 | 118–120 | 6.97 | 9.60 | 7.14 | 9.67 | 37.1,38.0 |
| m-NO$_2$C$_6$H$_4$CH= | 81 | 146–147 | 7.00 | 12.47 | 6.85 | 12.38 | 35.3,36.4 |
| o-HOC$_6$H$_4$CH= | 95 | 198–200 | 7.22 | 10.05 | 7.33 | 9.91 | 36.1,37.5 |

EXAMPLE 6

Synthesis of (2-N,N-dimethylaminoethoxy)-(p-N,N-dimethylaminophenyl)phosphinylacetohydrazide The reaction scheme B described hereinbefore is used to synthesise this compound starting from p-N,N-dimethylaminophenyldichlorophosphine.

EXAMPLE 7

Synthesis of [(2-chloroethoxy)(p-tolyl)phosphinyl] (hydroxyimino)acetohydrazide

The reaction scheme C described hereinbefore is used to synthesise this compound starting from p-chlorophenyldichlorophosphine and ethylene oxide.

EXAMPLE 8

Toxicity of CAPAH

It was established in the course of pharmacological investigation that 2-chloroethoxy(p-N,N-dimethylaminophenyl)-phosphinylacetohydrazide (CAPAH) is a biologically active substance which selectively affects the central nervous system. A comparison of the proposed compound with its nearest analogue in structure and purpose, diphenylphosphinylacetohydrazide (DPAH), has shown that CAPAH is a less toxic compound with a significantly greater interval between the maximum tolerance dose ("MTD") and the LD$_{100}$ than DPAH (Table 2).

TABLE 2

| Compound | LD$_{100}$ (mg/kg) | LD$_{50}$ (mg/kg) | MTD (mg/kg) |
|---|---|---|---|
| CAPAH | 1200 | 960 ± 35.0 | 700 |
| DPAH | 500 | 315 ± 24.8 | 200 |

EXAMPLE 9

Impact of CAPAH on Dopaminergic Activity (1) Interaction with apomorphine.

The effect of CAPAH on apomorphine-induced hypothermia and stereotypy was evaluated. The hypothermia was induced by subcutaneously injecting mice with 25 mg/kg of apomorphine. The change in skin temperature was recorded by a TPEM-1 thermometer immediately before injecting with apomorphine and also 60 and 120 minutes after the administration.

Figure 2:
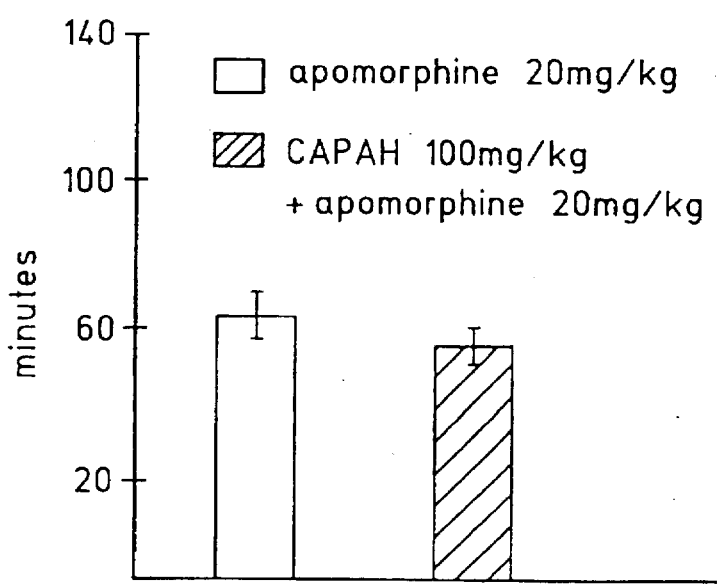
FIG. 2 shows the effect of CAPAH on apomorphine-induced stereotypy in rats.

Stereotypy in rats was induced by subcutaneous administration of 20 mg/kg of apomorphine. The total duration of the stereotypy episode was evaluated and also the intensity of individual components thereof (licking, gnawing, sniffing). CAPAH was administered 40 minutes before the apomorphine as a 90 mg/kg dose to the mice and 100 mg/kg dose to the rats. The results show no effect of CAPAH on apomorphine-induced effects (FIGS. 1 and 2).

(2) Interaction with L-dopa.

Figure 3:
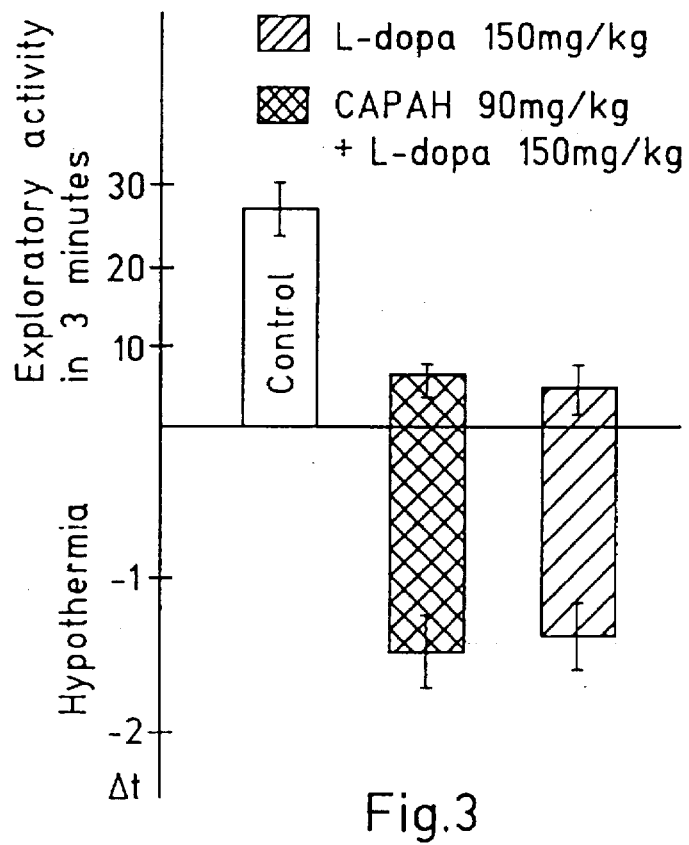
FIG. 3 shows the effects of CAPAH on L-dopa induced hypothermia and motor activity.

L-3,4-dihydroxyphenylalanine (L-dopa) was administered in a 150 mg/kg dose, which induces hypothermia, depression and reduction of motor activity. CAPAH administered in a dose of 100 mg/kg to mice showed no activity (FIG. 3).

(3) Impact on catalepsy caused by haloperidol.

Haloperidol in a vial was administered subcutaneously in a 5 mg/kg dose 40 minutes after the CAPAH (90 mg/kg).

Catalepsy was evaluated from the animal's ability to maintain an awkward posture (hind legs placed on a 30 mm high pedestal and forelegs on the bench) for 90 seconds at intervals of 10, 60 and 120 minutes after the latest administration of haloperidol.

Figure 4:
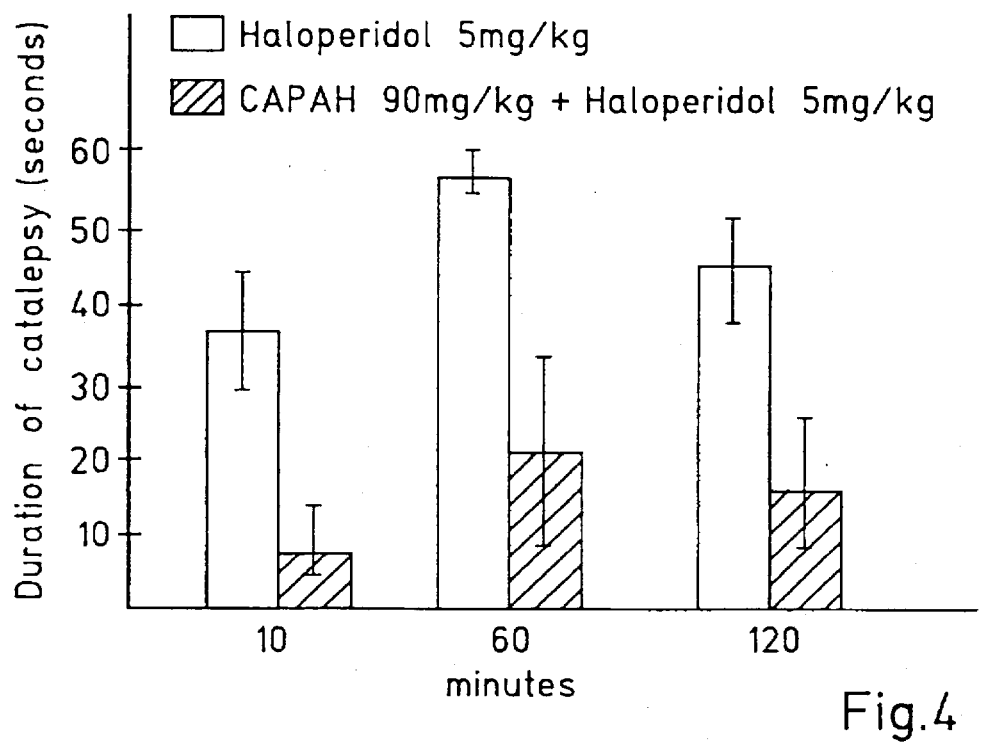
FIG. 4 shows the effect of CAPAH on haloperiodol-induced catalepsy.

The results are shown in FIG. 4.

EXAMPLE 10

Memory Enhancing Activity of CAPAH

The protective effect of the compound CAPAH was studied in relation to both scopolamine and hypoxia induced amnesia in gerbils by the passive avoidance test.

METHODS

Training Procedure

Gerbils underwent a training schedule of "passive avoidance", i.e. they learned not to enter a dark compartment into which an electric shock was delivered.

Scopolamine Induced Amnesia

Gerbils received an intra-peritoneal injection of scopolamine (0.5 mg/kg) 30 minutes before the training procedure. The ability of CAPAH, given prior to scopolamine, to prevent the induced amnesia was determined.

Hypoxia Induced Amnesia

The gerbils were trained as described above. To produce a hypoxic environment a gas-mixture (4% oxygen, 96% nitrogen) was blown through a plastic box (12 l/min). Immediately after the training period the gerbil was put into this hypoxic environment and removed when gasping was shown (maximum stay in the hypoxic box is 40 seconds).

Passive Avoidance Test

The gerbils were trained as described above in a step-down type passive avoidance apparatus (Model E13-08, Coulbourn Instruments, Lehigh Valley, USA), divided into a safe part and a grill part. The experimental chamber (16× 16×20 cm) had a safety platform (6×16×3 cm) and a floor made of stainless steel rods. Training of the passive avoidance was carried out for 5 minutes. The gerbils were placed on the safety platform and received a series of mild electric shocks, 0.12–0.2 nA (shock sensitivity determined for each batch of gerbils) for 3 seconds every $_6$ seconds when it stepped off the grill. Gerbils were returned to the apparatus for testing 24 hours later and their step-down latencies to the grill floor (recall latency) were recorded (maximum 60 seconds). Control animals had a high step-down latency.

In both these series of experiments Piracetam was used as a control.

RESULTS

The results are shown in Tables 3 and 4 below.

TABLE 3

Effects of CAPAH on hypoxia induced amnesia in the Mongolian Gerbil.

| Groups | n | Latency (sec ± SEM) |
|---|---|---|
| Control | 13 | 131 ± 16 |
| Hypoxia | 11 | 69 ± 17* |
| Piracetam (100 mg/kg) | 10 | 107 ± 19 |
| CAPAH | | |
| 1 mg/kg | 9 | 135 ± 21** |
| 10 mg/kg | 10 | 111 ± 25 |
| 30 mg/kg | 9 | 71 ± 28* |
| 100 mg/kg | 10 | 119 ± 23 |
| 300 mg/kg | 5 | 20 ± 8* |

Statistical Analysis: ANOVA followed by Dunnett t-test
*Significantly different from Control (p < 0.05)
**Significantly different from Hypoxia (p < 0.05)

In this test CAPAH is active in doses 1, 10, 100 mg/kg. Activity was absent in doses 30, 300 mg/kg. The dose of 300 mg/kg (⅓ DL50) is toxic. Probably, the mechanism of CAPAH positive effect in doses of 1, 10, 100 mg/kg is different. In the dose of 100 mg/kg CAPAH reveals dopamine-mimetic activity. This dose of the compound reduces haloperidol induced catalepsy (5 mg/kg—hypodermic injection).

CAPAH activity in small doses (1 and 10 mg/kg) may be caused by some other mechanism, for example a membrane related effect which may anticipate an intervention into metabolic processes on the cellular level.

TABLE 4

Effect of CAPAH on scopolamine induced amnesia in the Mongolian Gerbil.

| Groups | n | Latency (sec ± SEM) |
|---|---|---|
| Control | 13 | 117 ± 18 |
| Scopolamine (0.5 mg/kg) | 14 | 18 ± 6* |
| Piracetam (100 mg/kg) | 10 | 73 ± 24 |
| CAPAH | | |
| 1 mg/kg | 10 | 35 ± 17* |
| 10 mg/kg | 10 | 52 ± 21* |
| 30 mg/kg | 10 | 36 ± 17* |
| 100 mg/kg | 10 | 49 ± 16* |
| 300 mg/kg | 8 | 76 ± 30 |

Statistical Analysis: ANOVA followed by Dunnett t-test
*Significantly different from Control (p < 0.05)

Statistically significant reversal of scopolamine-induced amnesia was observed only at 300 mg/kg, although a trend towards memory enhancement was observed at the lower doses.

EXAMPLE 11

Anti-depressive Activity of CAPAH

To illustrate the anti-depressant activity of CAPAH, "behavioural despair" and "learned helplessness" models were used.

(A) Behavioural Despair Model

In this test, mice (tetrahybrids SVA) were obliged to swim in a limited space, presented as a cylindrical vessel which was 15 cm high containing a water level of $_6$ cm maintained at a temperature of 21° C. A "slowing down" of swimming activity was observed. This "slowing down" is regarded to reflect the state of lowering of spirits and increasing despair of the mice. The slowing down is diminished by anti-depressants.

CAPAH was investigated in acute and chronic application (for 10 days). The mean duration of animal immobility for 6 minutes of observation was estimated in seconds.

CAPAH was injected in a dose of 90 mg/kg 40 minutes before the experiment. The results of the experiment indicated that the repeated application of CAPAH lessens the duration of "slowing down" which is suggestive of anti-depressant activity.

The results are shown in Table 5 below.

TABLE 5

| CAPAH Influence on the Duration of Mice Immobilization According to "Behavioural Despair" Test | | |
|---|---|---|
| | Single Injection | Repeated Injection |
| Control | 225 ± 12.5 min. | 225.0 ± 12.5 |
| CAPAH | 210 ± 22.5 min. | 177.5 ± 17.5* |

*Significantly different from control (p < 0.05)

(B) Learned Helplessness Model

The phenomenon of learned helplessness is that exposure to uncontrollable stress produces deficits in subsequent learning tasks. The preliminary non-avoidable aversive phase of the test was carried out in dark chambers (30 cm×15 cm×15 cm) with electrodes in the floor. Mice were placed into the chambers individually where they received a number of stimuli (150 mkA, 60 Hz) for 6 seconds with 30 second intervals. Exposure lasted for 40 minutes. 24 hours later the animals were tested in a "shuttle" chamber which consisted of two compartments with the electrode floor connected by the opening situated 1 cm above the base. The entrance to the neighbouring compartment was blocked by a door operated automatically. Stimulation (150 mkA) was directed in turn to each compartment with 30 second intervals and 4 seconds lag. After 10 sessions the door was closed and electric current stopped. The average summary latent time of avoidance was estimated as well as the total number of non-fulfilled reactions.

Experiments were carried out in 40 male rats weighing 18–20 g. Melipramine was used as a standard preparation. Preparations were injected intraperitoneally in doses: CAPAH—90 mg/kg, melipramine—7 mg/kg. Control animals received an equal quantity of distilled water. In the first control group (control 1) mice were not exposed to non-avoidable aversive stimulations; in the second control group (control 2) the animals were exposed to the preliminary non-avoidable aversive influence but without drug preparations. During the next testing (in 24 hours) in a "shuttle chamber" the animals preliminary placed in the situation of non-avoidable stress displayed a real behaviour deficit preserved on repeated testing on the $_6$th and 12th days.

CAPAH (90 mg/kg) demonstrated marked anti-depressant effects, both after single and chronic treatment as shown in Table 6 hereinafter.

TABLE 6

| | | CAPAH Influence on Indices of "Avoidance Reaction" in Mice Subjected to Preliminary Nonavoidable Stress-Influence on "Learned Helplessness" Model | | | | | |
|---|---|---|---|---|---|---|---|
| Substances | Dose in mg/kg | Percent of nonavoidance from total test number | Average latence of avoidable period | Percent of nonavoidance from total test number | Average latence of avoidance period | Percent of nonavoidance from total test number | Average latence of avoidable period |
| | | single injection | | 6-fold injection | | 12-fold injection | |
| Control 1 | | 17% | 10.1 ± 1.3 | 16% | 9.5 ± 0.9 | 17% | 8.8 ± 1.0 |
| Control 2 | | 63%ˣ | 16.1 ± 1.6ˣ | 54%ˣ | 15.4 ± 1.7ˣ | 56%ˣ | 15.2 ± 1.5ˣ |
| CAPAH | 90 | 19** | 12.1 ± 1.5 | 2%** | 9.0 ± 0.7** | 1.3%** | 7.9 ± 0.7** |
| Melipramine | 7 | 43% | 13.5 ± 1.8 | 29% | 11.8 ± 1.5 | 11%* | 9.2 ± 1.1* |

ˣ = p < 0.05; ˣˣ = p < 0.01 concerning control 1 (unstressed mice)
* = p < 0.05; ** = p < 0.01 concerning control 2 (stressed mice)

EXAMPLE 12

Neuroprotective Activity of CAPAH

The potential of CAPAH to provide neuroprotection following a stroke was illustrated by its anti-hypoxic properties in mice using both hypoxia induced directly by lack of oxygen in the atmosphere and hypoxia induced by sodium nitrite injection.

(A)

White mice in groups of six with a standard weight of 18 grams were placed in hermetically sealed jars and the lifetime of the animals was recorded. A control group of mice received no pre-treatment whilst other groups received a prior intraperitoneal injection of 90 or 45 mg/kg CAPAH in one experiment, or 30 mg/kg of CAPAH in a second experiment (equivalent to about $\frac{1}{10}$, $\frac{1}{20}$ and $\frac{1}{30}$ of the $LD_{50}$).

The results obtained, as shown in Table 7, indicate an extension of lifetime when using 90 or 45 mg/kg of CAPAH.

TABLE 7

Effect of CAPAH on lifetime following hypoxia induced by direct lack of oxygen

| Treatment | Lifetime (± deviation) minutes |
|---|---|
| Control | 14.0 |
| 90 mg/kg CAPAH | 17.0 ± 0.1* |
| 45 mg/kg CAPAH | 18.8 ± 1.1* |
| Control | 16.2 ± 0.6 |
| 30 mg/kg CAPAH | 16.4 ± 1.2 |

*indicates statistically significant difference from control (B)
White mice in groups of eight with a weight in the range of 18 to 21 grams were injected subcutaneously with 300 mg/kg of aqueous sodium nitrite and their subsequent lifetime was recorded. A control group of mice received no additional pre-treatment but a second group received a prior intraperitoneal injection of 90 mg/kg CAPAH.

The results obtained, as shown in Table 8, indicate an extension of lifetime when using CAPAH.

TABLE 8

Effect of CAPAH on lifetime following hypoxia induced by sodium nitrite

| Treatment | Lifetime (± deviation) minutes |
|---|---|
| Control | 13.5 ± 1.2 |
| 90 mg/kg CAPAH | 16.9 ± 1.0* |

*indicates statistically significant difference from control

We claim:

1. A compound of formula (I):

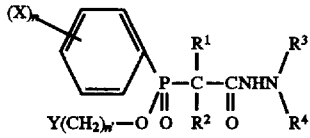

wherein each X separately is halogeno, hydroxy, $C_{1-4}$ alkyl, $C_{1-4}$ alkoxy, nitro or an unsubstituted or substituted amino group NRR' in which R and R' are each separately selected from hydrogen, $C_{1-4}$ alkyl groups and $C_{2-4}$ halogenated alkyl groups;

wherein Y is halogeno, hydroxy, $C_{1-4}$ alkoxy or an unsubstituted or substituted amino group NRR' in which R and R' are as defined above;

wherein n represents 0, 1, 2 or 3 and n' represents 1, 2, 3 or 4;

wherein $R^1$ and $R^2$ each separately represent hydrogen, halogeno, phenyl or a $C_{1-4}$ alkyl group, or together represent a group =NOR" in which R" is hydrogen or is a group ZC(O)— or (ZO)$_2$P(O)— where Z is a $C_{1-4}$ alkyl group; and wherein $R^3$ and $R^4$ each separately represent hydrogen, acetyl, phenyl, 2,2,2-trichloro-1-hydroxyethyl or a $C_{1-4}$ alkyl group, or together represent a group =CHR'" in which R'" is a $C_{1-4}$ alkyl, $C_{1-4}$ halogenated alkyl or phenyl group or represent a group =CH—CH=CHR'" in which R'" is as defined above, with any phenyl group present in $R^3$, $R^4$ or $R^3$+$R^4$ optionally being substituted by 1 to 3 groups selected from halogeno, hydroxy, $C_{1-4}$ alkyl, $C_{1-4}$ alkoxy, nitro and unsubstituted or substituted amino groups NRR' in which R and R' are as defined above; the compound optionally being in the form of a physiologically acceptable salt.

2. A compound according to claim 1, in which n is 1.

3. A compound according to claim 2, in which X is NRR'.

4. A compound according to claim 3, in which NRR' is a dimethylamino group substituted at the para position of the benzene ring with respect to the phosphorus-containing grouping.

5. A compound according to claim 1, in which Y is a halogeno group.

6. A compound according to claim 5, in which Y is chloro.

7. A compound according to claim 1, in which n' is 2.

8. A compound according to claim 1, in which $R^1$ and $R^2$ are each hydrogen.

9. A compound according to claim 1, in which $R^3$ and $R^4$ are each hydrogen.

10. A compound according to claim 1, in which $R^3$ and $R^4$ are a group =CHR'" or a group =CH—CH=CHR'" where R'" is methyl, phenyl, nitrophenyl or hydroxyphenyl.

11. A compound according to claim 1 being 2-chloroethoxy(phenyl)phosphinylacetohydrazide or a physiologically acceptable salt thereof.

12. A compound according to claim 1 being 2-chloroethoxy-(p-N,N-dimethylaminophenyl) phosphinylacetohydrazide or a physiologically acceptable salt thereof.

13. A compound according to claim 1 being other than 2-chloroethoxy-(p-N, N-dimethylaminophenyl) phosphinylacetohydrazide or a physiologically acceptable salt thereof.

14. A compound according to claim 1, which is in the form of a physiologically acceptable salt.

15. A compound according to claim 14 which is in the form of a hydrochloride salt.

16. A pharmaceutical composition comprising a compound according to claim 1 together with a physiologically accceptable diluent or carrier.

17. A pharmaceutical composition according to claim 16, in which the physiologically acceptable diluent or carrier is a sterile and pyrogen free liquid or a solid.

18. A pharmaceutical composition according to claim 16 which is formulated in unit dosage form.

19. A method for the treatment of a patient suffering from depression and/or in need of memory enhancement which comprises administering to said patient a therapeutically effective amount of a compound of formula (I) as defined in claim 1.

* * * * *